United States Patent
Nelson et al.

[11] Patent Number: 5,982,482
[45] Date of Patent: Nov. 9, 1999

[54] DETERMINING THE PRESENCE OF DEFECTS IN THIN FILM STRUCTURES

[75] Inventors: Keith A. Nelson, Newton, Mass.; John A. Rogers, New Providence, N.J.

[73] Assignee: Massachusetts Institute of Technology, Cambridge, Mass.

[21] Appl. No.: 08/903,901

[22] Filed: Jul. 31, 1997

[51] Int. Cl.$^6$ ............................................. G01N 29/04
[52] U.S. Cl. ................................. 356/237.1; 73/643
[58] Field of Search .................................. 356/237, 432, 356/237.1; 73/643

[56] References Cited

U.S. PATENT DOCUMENTS

| | | | |
|---|---|---|---|
| 4,541,280 | 9/1985 | Cielo et al. | 73/662 |
| 4,581,939 | 4/1986 | Takahashi | 73/643 |
| 4,710,030 | 12/1987 | Tauc et al. | 356/432 |
| 5,344,236 | 9/1994 | Fishman | 356/237 |
| 5,672,830 | 9/1997 | Rogers et al. | 73/597 |

OTHER PUBLICATIONS

Rogers, "In–Plane Acoustic Echoes," *Time–Resolved Photoacoustic and Photothermal Measurements on Surfaces, Thin Films and Multilayer Assemblies*, May 1995, pp. 36–40.

*Primary Examiner*—Richard A. Rosenberger
*Attorney, Agent, or Firm*—Fish & Richardson P.C.

[57] ABSTRACT

The invention features a method for detecting a subsurface defect in a thin film structure. The method includes: optically generating an acoustic wave in a first spatial region of the film; optically measuring a time-dependent reflection of the acoustic wave from subsurface features in the film to produce a time-dependent signal; and analyzing the signal to detect an existence of the defect. The optically measuring step can include measuring the diffraction of a probe beam from the reflected acoustic wave. The analyzing step can include comparing the measured signal to a reference signal for defect-free structure.

16 Claims, 5 Drawing Sheets

DETERMINING THE PRESENCE OF DEFECTS IN THIN FILM STRUCTURES

STATEMENT AS TO FEDERALLY SPONSORED RESEARCH

This invention was made with Government support under DMR-900279 awarded by the National Science Foundation. The Government has certain rights in the invention.

BACKGROUND OF THE INVENTION

The invention relates to an optical method for detecting the presence of defects in thin films.

Thin metal, polymer, and semiconductor films are common in microelectronic, optical, biomedical, and aerospace devices. They are typically intricate devices with many microscopic features. For example, in a silicon wafer there may be vertical "posts" of metal running through the insulating oxide layers, providing electrical connections between different metal layers. Also common are "trenches" filled with metal embedded within the oxide layers. In any case, during or after fabrication steps, defects in the desired features may occur. For example, a trench may not have been properly etched or may not be completely filled with metal. A post may be unfilled, leaving a void rather than a conducting region. Such defects will limit the performance of the final device, in some cases making them inoperable.

Ideally, a defect is detected before the device containing the defect is completed. This prevents unnecessary processing of the defective device, thereby saving time and money. Furthermore, the causes of defects can be more easily determined once the defects are detected and characterized. However, defects are usually buried within devices making their detection difficult.

SUMMARY OF THE INVENTION

The invention features a method for optically determining the presence and location of defects in thin film structures.

In general, in one aspect, the invention features a method for detecting a subsurface defect in a thin film. The method includes: optically generating an acoustic wave in a first spatial region of the film; optically measuring a time-dependent reflection of the acoustic wave from subsurface features in the film to produce a time-dependent signal; and analyzing the signal to detect an existence of the defect.

Embodiments of the invention can include any of the following features. The generating step can include any of producing counter-propagating acoustic waves, exciting the film with a pair of crossed laser pulses, or passing a beam through a mask to produce a spatially periodic pattern of excitation light on the film. The crossed laser pulses can have pulse durations of less than about 1 ns or less than about 150 ps. The measuring step can include detecting light diffracted by the reflection. Also, the reflection in the measuring step can be measured at the first spatial region. The analyzing step can include comparing the signal to a reference signal for a defect-free film. The method can further include determining the position of the defect from the signal.

In this technique, the optical excitation of the films induces acoustic waveguide responses in the film of a thin film structure. A probe beam is used to monitor these responses. The responses diffract the probe beam to produce a diffracted beam, which is measured by a detector. The light-induced signal provided by the detector includes information about acoustic waves propagating along the thin film structure. This signal is analyzed to determine the presence of defects in the thin film structure. The analysis includes a comparison to the signal produced by a thin film structure known to be defect-free. The signal data is collected in a matter of seconds with a high signal-to-noise ratio, making the measurements rapid and highly accurate.

Because the film measurement method is both fast and accurate it can be used, for example, in-line during semiconductor wafer processing to determine the presence of defects in film-containing wafers. When measured during processing, devices having defects are rejected. If there is a systematic presence of defects, processing is halted and the defective film-containing devices are more carefully characterized to determine and correct the cause of the defects. As a result, the method allows production of higher-quality films and prevents further processing of defective wafers. Also, the method is non-destructive.

Other features, aspects, and advantages follow.

DETAILED DESCRIPTION

Figure 1:
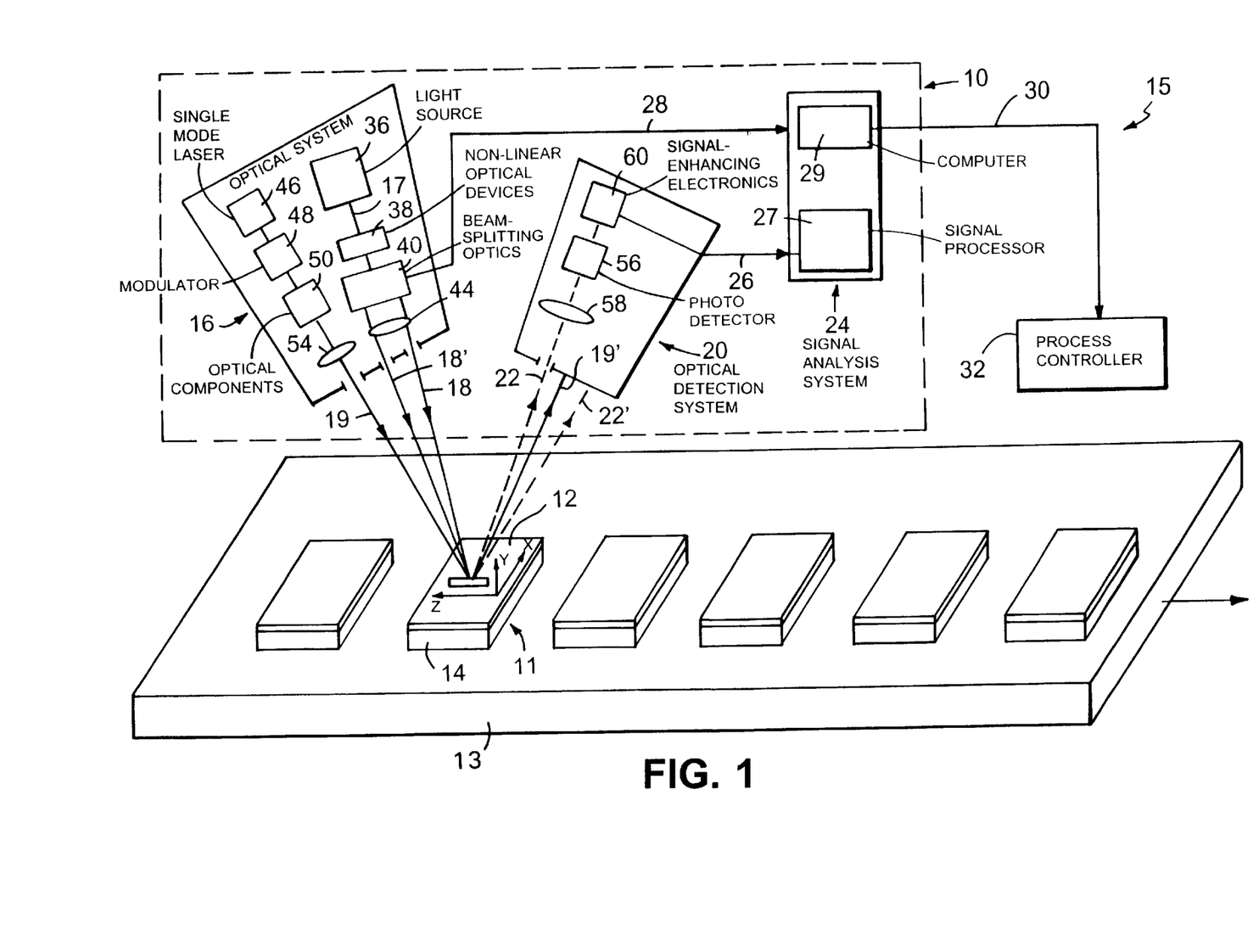
FIG. 1 is a schematic of a film-measuring device implemented in a device assembly line.

Referring to FIG. 1, a fabrication line 15 for processing a series of thin film structures 11 includes a film-measuring device 10 that allows the presence of defects in a thin film 12 of structure 11 to be accurately determined in a rapid, non-invasive manner. The film-measuring device 10 includes an optical system 16 for generating and directing excitation beams 18 and 18' and a probe beam 19 toward the surface of film 12. A spatially periodic, time-dependent optical intensity pattern, caused by optical interference between the excitation beams in the film, excites coherent waveguide modes. These modes include coherent counter-propagating acoustic waves that travel in the plane of the film and partially reflect from subsurface structures within the film. The probe beam 19 is used to irradiate a portion of the film surface and detect the reflected acoustic wave, which can diffract the probe beam. A diffracted portion 22 (or, alternatively, portion 22') of the probe beam 19 is detected using an optical detection system 20. The time-dependent intensity of the diffracted beam carries information about the reflected acoustic waves travelling through the region irradiated by the probe beam. This information, in turn, includes information about subsurface structure within the film, including the presence of defects. The detection system 20 generates a light-induced signal 26, which is then input to a signal-analyzer 24. The signal analyzer includes a high-bandwidth analog-to-digital converter 27 and a computer 29. The converter digitizes signal 26 into a digitized waveform that is sent to computer 29 for analysis.

Signal analyzer 24 analyzes light-induced signal 26 to determine the presence and location of defects in thin film 12. To do this, analyzer 24 compares signal 26 to a reference signal corresponding to the light-induced signal for a thin film structure known to be defect-free. Significant differences between the signals indicate the presence of defects. If defects are detected, computer 29 identifies the times at which the signals differ from one another. Using these times, analyzer 24 estimates the positions of the defects. Then, a movable table 13 translates the position of film 12 relative to probe beam 19 so that the probe beam irradiates the estimated location of one of the defects and a second signal is measured. Analysis of the second signal, which will be described below, determines if the estimated location of the defect is correct. If the estimated location of the defect is incorrect, the film measuring device makes additional measurements until the location of the defect is confirmed.

After the analysis, signal analyzer 24 generates a status signal 30 indicating the presence of defects or lack thereof and sends the status signal to a process controller 32, which may reject thin film structure 11 and alert an operator.

The effective area of thin film structure 11 measured by device 10 when signal 26 is recorded is limited by acoustic damping. In many materials, acoustic waves propagate on the order of 1 mm before being damped out. Therefore, for thin film structures having much larger dimensions (e.g., eight to twelve inches for semiconductor wafers), film measuring device 10 records signals from multiple locations of structure 11. Device 10 includes an automatic positioning system (not shown) for identifying locations of structure 11 irradiated by the excitation and probe beams and directing movable table 13 to position structure 11 to desired locations relative to the excitation and probe beams. Automatic positioning systems are well known in the art, and can include, for example, a vision system for imaging the surface of film 12. The automatic positioning system insures that device 10 only measures important regions of the film, i.e., regions that may have defects detrimental to the desired function of the structure. Computer 29 stores references signals for each of the locations measured by film measuring device 10 and uses these references signals to analyze the measured signals. The number of locations measured for a given thin film structure will depend on the redundancy of the features within the structure and the degree of confidence required for determining the quality of the structure.

Figure 2:
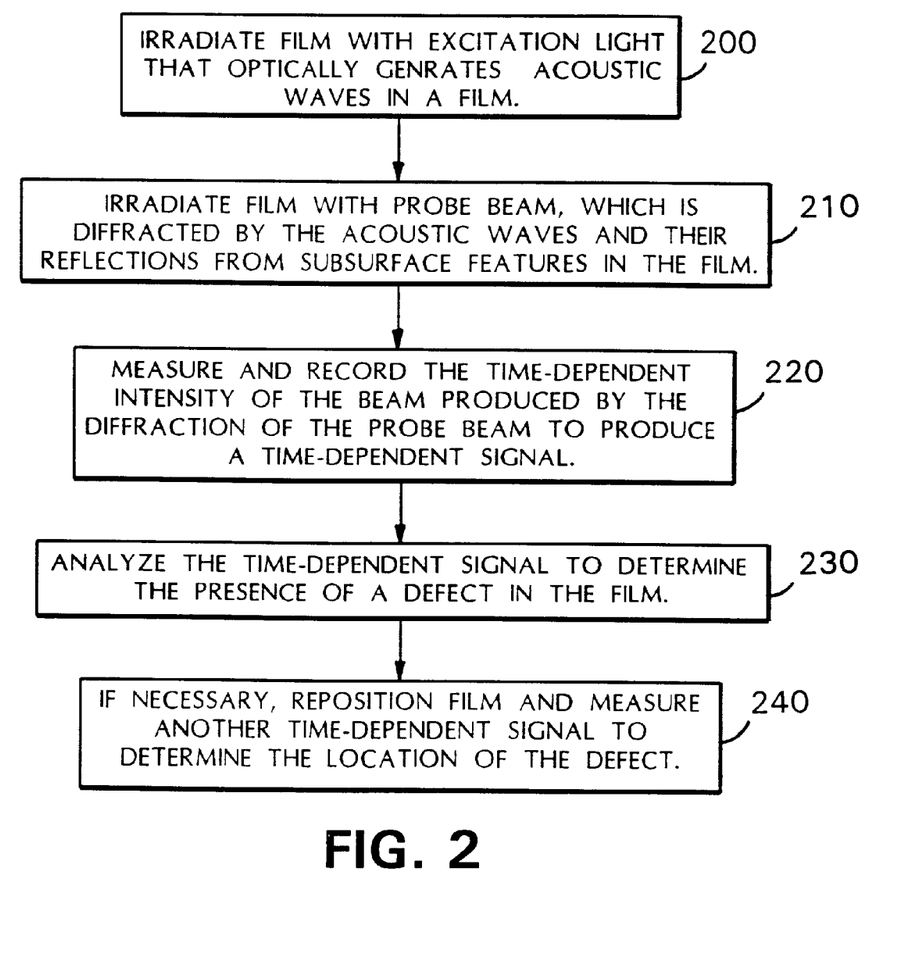
FIG. 2 is a flow chart of the process used for determining the presence of defects in a film-containing device.

Referring to FIG. 2, each measurement involves the following steps, each of which will be described in further detail below. First, optical system 16 irradiates film 12 with excitation light that optically generates acoustic waves (step 200), and also irradiates film 12 with a probe beam, which is diffracted by the acoustic waves and their reflections from subsurface features in the film (step 210). Optical detection system 20 measures the time-dependent intensity of the beam produced by the diffraction of the probe beam and sends signal 26 corresponding to that measurement to signal analyzer 24 (step 220). Then, signal analyzer 24 analyzes signal 26 to determine the presence of a defect in thin film structure 11 (step 230). Finally, if necessary, movable table 13 repositions structure 11 and film measuring device 10 repeats steps 200–230 to confirm the location of the defect (step 240).

Optically Generating and Detecting Acoustic Waves

Optical system 16 generates acoustic waves in thin film 12 by impulsive stimulated thermal scattering (ISTS). In ISTS, two crossed picosecond laser pulses form an interference or "grating" pattern of alternating peaks and nulls. Optical absorption and sudden heating at the peaks causes thermal expansion there, resulting in generation of an acoustic response whose geometry matches that of the grating pattern. The acoustic waves are detected through time-resolved diffraction of a probe laser beam. The diffracted signal shows time-dependent oscillations and decay, directly revealing the acoustic frequency and damping rate. A detailed description of ISTS optical systems is given in J. A. Rogers et al., J. Appl. Phys. 75:1 (1994) and A. R. Duggal et al., U.S. Ser. No. 07/910,762, the contents of which are incorporated herein by reference.

An alternate, usually weaker excitation mechanism, impulsive stimulated Brillouin scattering (ISBS), may also contribute to acoustic wave generation. For this mechanism, absorption of the excitation pulse wavelength by the sample is not necessary.

Figure 3:
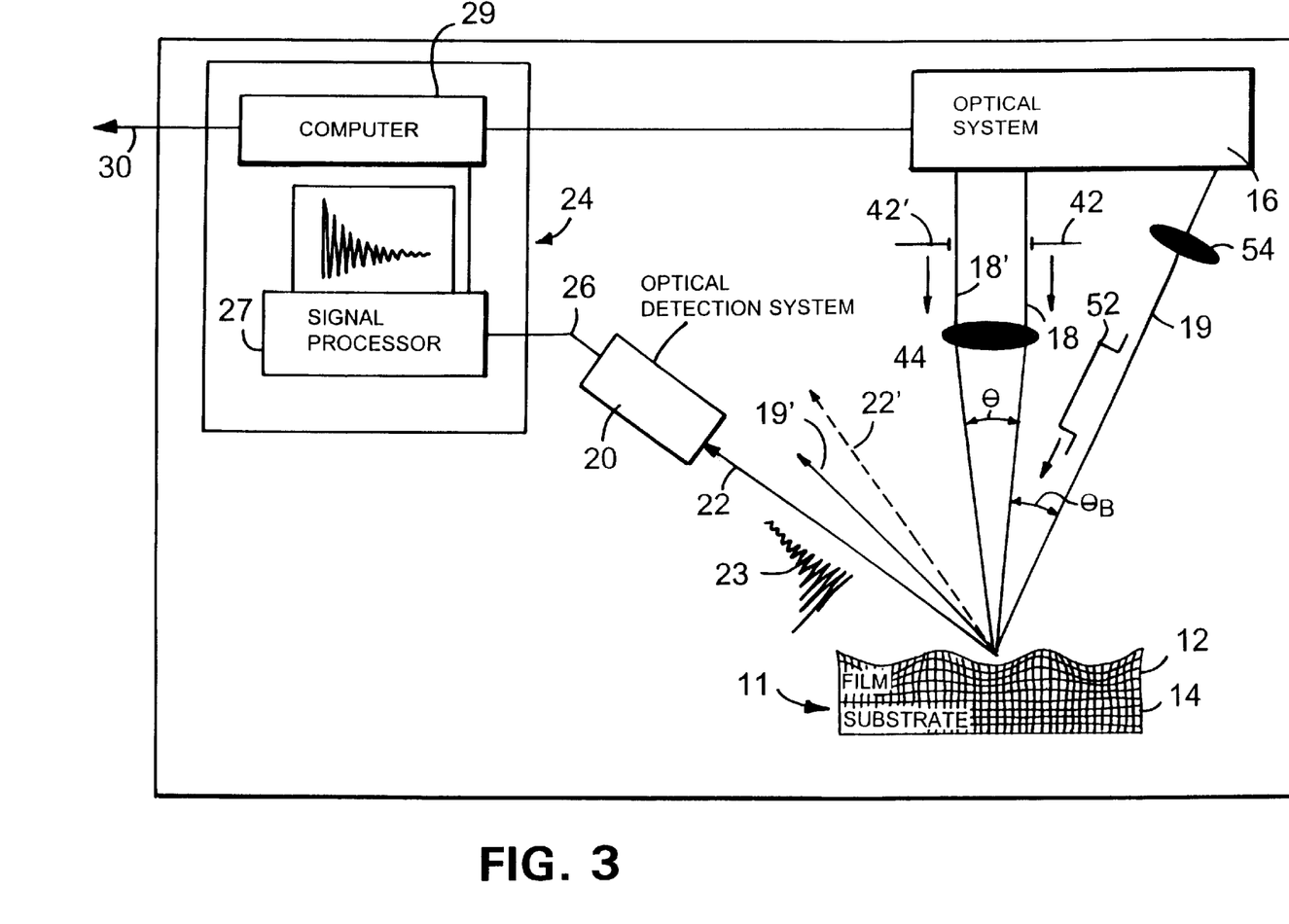
FIG. 3 is a schematic of a film-measurement device used for optically exciting and detecting acoustic waves in a thin film.

Referring to FIGS. 1 and 3, optical system 16 includes an excitation light source 10 used to generate an optical beam 17 containing an excitation pulse. If the carrier frequency of the excitation pulse is below the frequency corresponding to the absorption energy of the film, the optical beam 17 is processed by one or more non-linear optical devices 38, such as a frequency-doubling or frequency-tripling crystal, which generates higher-order harmonics (e.g., second or third harmonics) of the fundamental frequency. When the excitation pulse is of suitable frequency, a series of beam-splitting optics 40 process the pulse to generate two excitation beams 18, 18', each containing pulses 42, 42'.

Lens 44 focuses and directs the excitation beams onto the film so that they overlap with one another spatially. The excitation beams also have substantially identical path lengths so that they overlap with one another in time. Optical interference between the overlapped pulses produces a spatially varying intensity pattern, or grating. This optical grating is absorbed producing local heating and thermal expansion at the peaks of the grating (i.e., ISTS). The expansion produces an acoustic response whose geometry matches that of the grating pattern. The acoustic response includes coherent counter-propagating waveguide modes, indicated in FIG. 3 by the spatial displacements in the film. These modes give rise to a time-dependent signal 23 including a damped oscillatory component. In addition to the propagating acoustic modes, the optical grating induces a quasi-steady-state material response that persists until thermal diffusion washes out the temperature grating.

The acoustic wavelength of the acoustic waves generated by the crossed excitation beams is an important parameter for detecting subsurface features and defects. The wavelength depends on the angle θ between the excitation beams and on the wavelength $\lambda_1$ of the excitation beams. In particular, the acoustic wavelength Λ and acoustic wavevector magnitude q are given by the equation $q=4\pi(\lambda_1)^{-1} \sin(\theta/2)=2\pi/\Lambda$. In general, short acoustic wavelengths will be most sensitive to features close to the surface of the film, while longer acoustic wavelengths will also probe features deeper within the film. The total depth probed is roughly equal to the acoustic wavelength, which for optical excitation wavelengths of about 100 nm to 1000 nm is about 0.1 to 100 microns. The damping rates of the acoustic waves will also depend on the acoustic wavelength.

Another important parameter is the duration of the excitation pulses. To excite acoustic waves, the duration of the excitation pulses must be smaller than the acoustic period of the acoustic waves. The acoustic period for a particular mode will also depend on its wavelength. Typically, the duration of the excitation pulses is less than 1 ns, and sometimes less than 0.1 ns.

The spot size of the excitation pulses is also an important parameter. The initial geometry of the excited acoustic waves match the rapid thermal expansion induced by the excitation pulses. Therefore, the excitation pulses generate counter-propagating acoustic wavepackets having widths comparable to the excitation spotsize along the direction of the grating. The acoustic wavelength of the wavepackets correspond to the fringe spacing of the grating. If the spot size along the grating is small, the wavepackets will propagate out of the excitation region quickly. If the spot size along the grating is large, the wavepackets will propagate at the same speed as in the case of the small spot size, but the wavepackets will remain, at least partially, in excitation region for a longer amount of time.

As the acoustic wavepackets propagate, they will encounter partially reflective boundaries in the film corresponding to subsurface features in the thin film structure. Initially, the reflected wavepacket and the original wavepacket will interfere with one another. In other words, the front of a wavepacket may reflect from a feature and counter-propagate through the back of the original wavepacket. Thereafter, the reflected wavepacket may interfere with other partially reflected wavepackets. These interferences and reflections implicitly include information about the location of subsurface features in the thin film structure. Moreover, if one or more of the subsurface features in a structure are defects, the reflections and interferences in that structure will be different than in a defect-free structure.

Optical detection system 20 records the time-dependent properties of the reflected and interfering acoustic waves by monitoring the time-dependent diffraction of the probe beam 19. The probe beam is produced by a continuous wave (cw) or quasi-cw laser 46. A modulator 48 electro-optically modulates the output of the laser to provide a well-defined probe waveform 52, usually a square wave, of duration sufficient to monitor the entire sample response of interest, i.e., longer than the acoustic damping time. Thereafter, the probe beam passes through or reflects off of additional optical components 50, such as mirrors, frequency and spatial filters, frequency-doubling crystals, or telescoping lenses, to achieve the desired spatial, energy, and intensity profiles. In order to sample the induced displacements on the surface on the film, lens 54 focusses the probe pulse 52 on the film. Alternatively, a single lens may be arranged to focus the excitation 18, 18' and probe 19 beams.

A time-resolving photodetector 56 housed in the optical detection system 20 detects the diffracted probe waveform 22. Thus, system 20 measures the entire time dependent response of the irradiated region of film with a single probe waveform. For especially weak signals, a lens 58 may be used to focus the diffracted beam on the optically active region of the detector 56, thereby increasing the intensity of the signal. For particularly noisy or weak signals, signal-enhancing electronics 60, such as high-speed amplifiers, may be used with optical detection system 20.

In some cases, the time resolution needed may exceed that obtainable with standard detection electronics. For example, it may be desirable to excite and monitor acoustic waves with frequencies in the 10–50 Ghz range. This demands time resolution on the order of 10 picoseconds or less for the highest frequencies. An alternate method of detection is to use of a probe pulse rather than a quasi-cw beam. The probe pulse is generated by partial reflection of the original output from excitation source 36, and has a different wavelength or polarization than the excitation pulses so that scattered light from the excitation pulses is filtered before it reaches optical detection system 20. The probe is variably delayed along a mechanical delay line (not shown) such that it reaches the sample at a variable delay following the excitation pulses. Photodetector 56 detects diffracted beam 22 as before. In this method, the time resolution is limited only by the probe pulse duration, i.e., photodetector 56 and electronics 60 need not have high time resolution. Optical detection system 20 measures the time-dependent signal by detecting diffracted light at many probe delay times and sending the diffracted light intensity for each delay to signal analyzer 24, with the total range of delay times sufficient to permit the entire response to be viewed.

In either case, since optical detection system 20 measures diffraction of probe beam 19 by the optically excited acoustic waves, the spot size of the probe beam must be larger than the acoustic wavelength of these waves and is typically larger than three to four acoustic wavelengths.

In one embodiment, the spot size of the excitation beams along the direction of the grating is small enough (e.g., about 10 to 100 microns) that the acoustic wavepackets propagate a significant distance (e.g., 1 mm) from the excitation region before being damped out. These wavepackets will reflect from features both inside and outside of the excitation region producing acoustic wave reflections or "echoes". The original wavepackets and the reflections will propagate through the region irradiated by the probe beam, which may or may not be inside the excitation region. If the probe beam irradiates the excitation region, the diffracted beam will include a contribution from the quasi-steady-state material response, which will heterodyne to the contribution from the original and reflected acoustic waves. The spot size of the probe beam is chosen to optimize spatial resolution while maximizing diffraction efficiency. In this embodiment, it is typically comparable to or smaller than the spot size of the excitation beams.

In another embodiment, the spot size of the excitation beams along the grating is larger enough (e.g., about 1 mm) that the acoustic wavepackets remain substantially within the excitation region before being damped out. Acoustic wave reflections will occur within the excitation region producing multiple interferences. The probe beam irradiates a relatively small region (e.g., about 10 to 100 microns) within the excitation region to monitor these interferences at a specific location. The interferences will produce characteristic beating patterns in the time-dependent diffraction signal that are indicative of a reflective feature. Again, the spot size of the probe beam is chosen to optimize spatial resolution while maximizing diffraction efficiency.

In this embodiment, there are different advantages to having the probe beam irradiate near the center or edge of the excitation region. If the probe beam irradiates a location near the center, signal should be stronger since acoustic waves from the entire excitation reach the center more quickly than if the probe beam irradiates an edge. However, if the probe beam irradiates the edge, the location of features is more easily interpreted from the signal since all of the acoustic waves are approaching the probe beam from the same side.

While the acoustic wavepackets counter-propagate along the direction of the grating, the spot sizes of the excitation and probe beams transverse to the grating should also be considered. If the excitation spot size is too big, the local intensity of the excitation pulses may be too small to generate acoustic waves with large enough amplitude. If the excitation spot size is too small, the acoustic waves may diverge along the direction transverse to the grating complicating the measurement. Typically, the excitation spot size along the dimension transverse to the grating is about 20 to 200 microns. The larger the spot size of the probe beam transverse to the grating, the greater the area of the film monitored by the method. However, if the spot size is too large, features and defects having dimensions much smaller than this spot size will produce acoustic reflections that diffract only a small portion of the probe beam, reducing the dynamic range of the measurement. Typically, the probe spot size along the dimension transverse to the grating is about 10 to 100 microns.

Analyzing the Measured Signal

Signal analyzer 24 in film measuring device 10 analyzes measured signal 26 from optical detection system 20 to determine the presence and location of a defect. First, analyzer 24 compares signal 26 to reference signal 28, which is stored in analyzer 24 in advance.

In some embodiments, the reference signal is calculated, either theoretically or numerically, from the design of the desired thin film structure. In other cases, film measuring device 10 measures the signal for a reference structure that is known to be defect-free, and that measured signal is stored in analyzer 24 as the reference signal. This signal is a signature of a defect-free device. To determine in advance that the reference structure is defect free, it can be characterized by other nondestructive techniques such as optical pattern recognition, destructive evaluation such as scanning electron microscopy (SEM), or electrical testing of a device after fabrication is complete. Several reference structures may be examined and then characterized independently so that the reference signal is determined reliably and that the defect-free nature of the reference sample is confirmed by the similarity among different reference signals. It is important that the reference and subsequent sample structures be reliably positioned relative to the excitation and probe beams as film measuring device 10 measures signal 26 so that acoustic responses from each of the counterpropagating acoustic wavepackets can interfere reproducibly with one another and yield reproducible signals.

To compare the responses, analyzer 24 normalizes the measured response to the reference response to account for variations in the optical sources. Then, the difference in signal intensity between the responses at corresponding time delays are determined. These differences are squared and then summed together to give an effective value for the similarity between measured response and the reference response (where a value of zero indicates an identical response). Even if the test structure (i.e., a device subsequent to the reference device) is substantially identical to the reference structure, the effective value might still take on a non-zero value because of noise and accuracy limitations. The signal-analysis system compares the effective value to a preset value. If the effective value is greater than the preset value, the test structure is considered to have a defect, otherwise the test structure is considered to be substantially identical to the reference structure, i.e., defect free. The preset value is set according to noise and accuracy limitations and can be optimized according to the effective values of test structures believed to be defect-free.

In another embodiment, after the measured response is normalized, the Fourier transform (FT) of the normalized measured response is calculated. This FT is compared to a FT of the reference response. The FT's will in general have complex values. Similar to the embodiment above, the sum of the (absolute) squares of the differences between the measured FT and the reference FT at corresponding points (which in this case are frequencies) give an effective value for the test structure that can be compared to a preset value to indicate if the structure is defect-free.

In both of the embodiments, the responses or the FTs of the responses can be filtered before calculating the effective value. For example, selected portions of the (time-domain) responses can be weighted before the calculating differences between the test and reference responses. Therefore, if structural features that potentially contain defects give rise to signatures (e.g., echoes or interference patterns) within a certain time window, that window can be weighted more heavily than other time windows in the responses. It might also be desirable to give zero weight to time windows corresponding only to background signal (i.e., no acoustic reflection information). Similarly, selected portions of the FTs of the responses can be weighted to emphasize frequencies corresponding to the acoustic wavepackets and reflections. Furthermore, high frequencies corresponding to noise and low frequencies corresponding to background signal can be given zero weight.

Many other methods for comparison of measured and reference signals can be used, including combinations of time-domain and FT analysis. In addition, signals derived from different measurement conditions such as different acoustic wavelengths or excitation or probe positions or spot sizes may be analyzed and compared to corresponding reference signals.

Once analyzer 24 has determined the presence of a defect in a test structure, it determines the location of the defect. Analyzer identifies the time delays (i.e., the time interval between the excitation pulses and a particular feature in the signal) at which the measured signal differs significantly from the reference signal. For example, the measured signal may include echoes that are either not present or distinctly different (e.g., in amplitude) than echoes in the reference signal, the analyzer identifies the time delays of these echoes. In general, differences in the signal between the measured and reference signals correspond to reflections from defects in the test structure that are not present in reference structure. By knowing the speed of the acoustic wavepacket, the analyzer can estimate the relative distances of the defects from these time delays. This analysis assumes that the largest differences between the signals (i.e., the ones for which time delays are identified) will correspond to single, rather than multiple, reflections from defects.

The analysis depends on the relative spot sizes and positions of the excitation and probe beams. If the excitation region is large (e.g., about 1 mm), the analyzer identifies the time delays at which the differences between the measured and reference signals just begin. These time delays correspond to the travel time for an acoustic wave that immediately encounters a defect in the excitation region to reflect from the defect and travel to a region irradiated by the probe beam. The analyzer then estimates possible locations of defects that are consistent with these time delays. To confirm the location of a defect, the movable table repositions the test substrate so that the probe beam irradiates the estimated location of the defect and the film measuring device measures another signal from the test substrate. If the estimated location of the defect is correct, this measured signal will include a signature of the defect at a time delay near zero (within a couple of acoustic periods). The movable table repositions the test substrate until the analyzer confirms the locations of all of the defects.

If the excitation region is small enough that acoustic wavepackets travel out of the excitation region, time delays corresponding to the differences between the measured and reference signals give the travel time for an acoustic wave to travel from the excitation region to a defect and reflect back to the region irradiated by the probe beam. Again, the analyzer estimates possible locations of defects that are consistent with these time delays. To confirm the location of a defect, the movable table repositions the test substrate so that the probe beam irradiates the substrate on one side of the estimated location of the defect and the film measuring device measures the signal from the test substrate. The measurement is then repeated with the probe beam irradiating the other side of the estimated location. If the probe beam is irradiating the location of the defect, the two signals will be significantly different from one another. One signal will include a signature corresponding to a reflection from the defect, while the other signal will include a signature corresponding a wavepacket transmitted partially through the defect. Again, the movable table repositions the test substrate until the analyzer confirms the locations of all of the defects.

Alternatively, in either of the above cases, the analyzer can estimate locations of defects from measurements of the test substrate at multiple positions. The analyzer determines the correct locations by identifying the estimated locations that are self-consistent with the multiple measurements.

In other embodiments, optical system 16 scans the position on the film of the probe beam relative to the excitation beams, and detection system 20 measures diffraction of the probe beam at each one of these positions. As above, analyzer 24 analyzes these measurements to determine the presence and location of defects.

Example of Optically Generating and Detecting Acoustic Waves

The following example illustrates optical generation of an acoustic wave and optical detection of a reflection of the acoustic wave from a known subsurface feature in a thin film structure.

Acoustic wavepackets were generated and reflections detected in a polyimide thin film supported by a silicon substrate having an opening beneath a portion of the film. As a result, the film had a tightly bound region (i.e., the region adhered to the substrate) and a delaminated region (i.e., the regions above the opening). The excitation and probe beams were focussed to about 40 microns in the delaminated region and overlapped with one another. The reflecting boundary in the film consisted of the interface between the bound and delaminated regions. In particular, there is a large acoustic impedance mismatch between these two regions.

Figure 4:
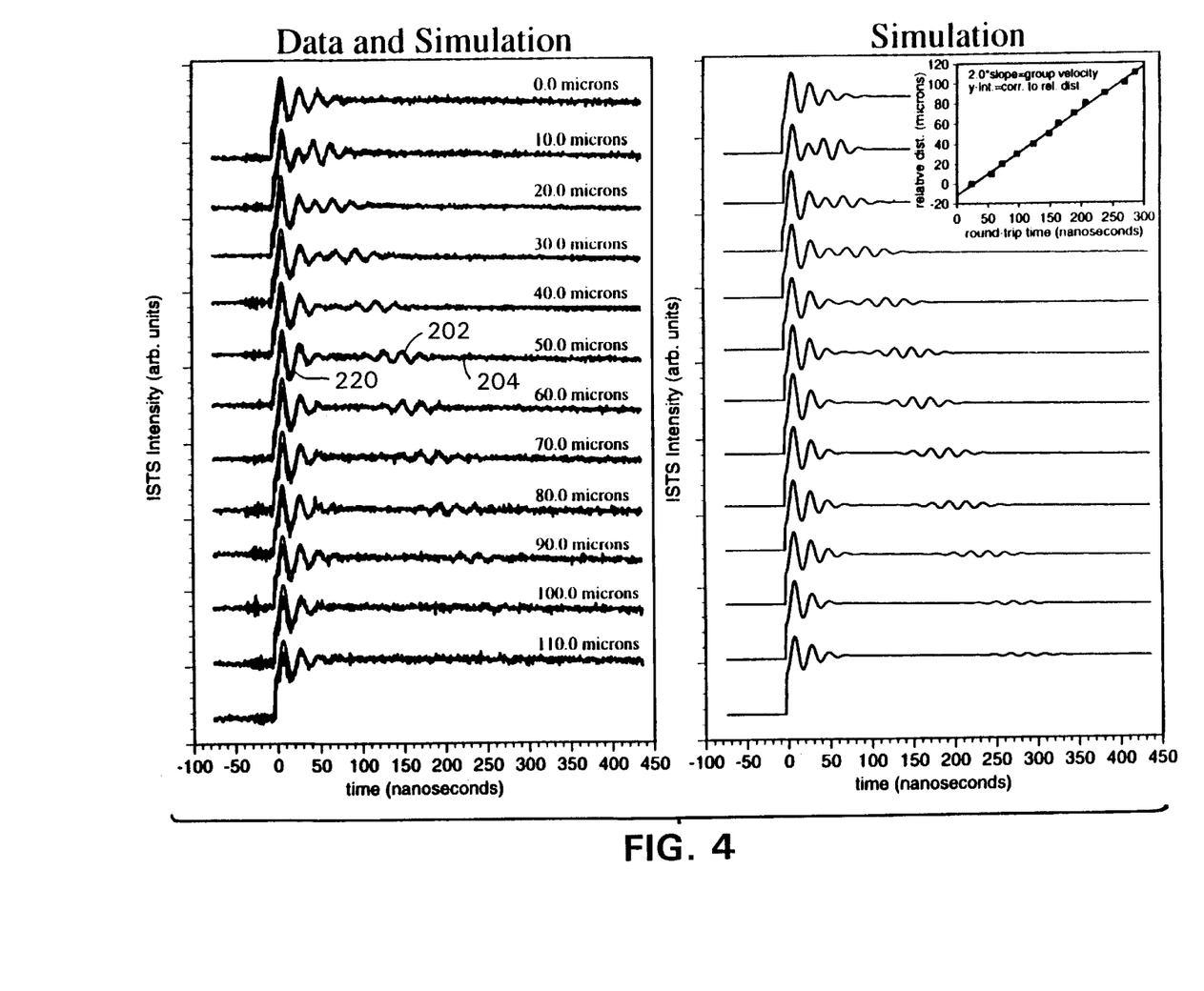
FIG. 4 is a series of plots of time-dependent diffracted signals measured using the film-measuring device along with numerical simulations.

Referring to FIG. 4, data along with numerical simulations are shown for a series of experiments in which the relative distance from the excitation region to the reflective boundary was varied. The data and simulations show the initial acoustic wavepacket 200 and the reflection 202 returning at a later time. Both of these oscillating responses ride on the quasi-dc thermal response 204. The distances in FIG. 4 are relative and do not represent absolute distances to the reflective boundary. The frequency of the acoustic oscillations determines the phase velocity.

In this example, the film was excited using a Q-switched, mode-locked, and cavity-dumped Nd:YAG laser. The output pulse had an energy of 1 millijoule, a wavelength of 1064 nm, a pulse duration of 100 ps, and a repetition rate of up to 1 KHz. The light from this laser was first attenuated and then passed through a lithium triborate (LBO) crystal to yield light at 532 nm, which was then mixed with the remnant 1064 nm radiation in a β-barium borate (BBO) crystal to yield excitation pulses of approximately 20 microjoules at 355 nm. This light was attenuated to yield ~1 microjoule pulses that were used for excitation of the films. During excitation, the 355-nm pulses were passed through a 50% beam splitter and then crossed at the angle θ. The excitation pulses were focussed using a spherical lens.

The probe pulse overlapped with the excitation pulses and was derived from a cw single-mode Argon ion laser (Lexel 3500) producing 1 Watt at 514 nm with a flat intensity profile. This output was electro-optically modulated (Conoptics 380) to yield a square pulse having a temporal width of between 1 and 20 microseconds. The probe beam was focussed to a spot of between 50 and 70 microns in the film. The diffracted component of the probe beam was measured with a fast amplified photodiode (Antel—2 Ghz bandwidth). The light-induced signal was then sent to a transient digitizer (Tektronics DSA 602A—1 Ghz bandwidth), resulting in generation of digital signal for analysis. The combination of the photodiode and transient digitizer effectively provided a 1 Ghz-bandwidth window through which film oscillatory and relaxational motions were monitored.

Example of Determining the Presence of Defects

Figures 5A, 5B:
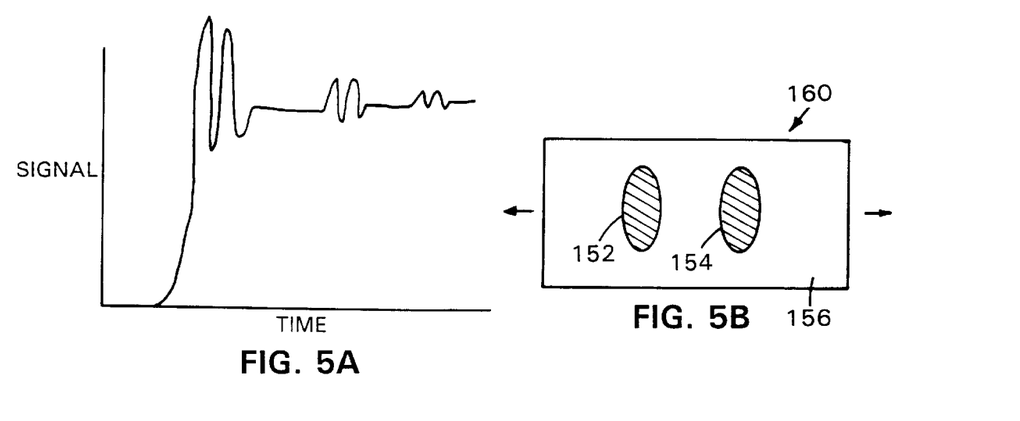
FIGS. 5A–5F are plots (FIGS. 5A, 5C, and 5E) of a optically measured time-dependent responses to acoustic excitation and cross-sectional views (FIGS. 5B, 5D, and 5F) of a multilayer semiconductor devices.
Figures 5C, 5D:
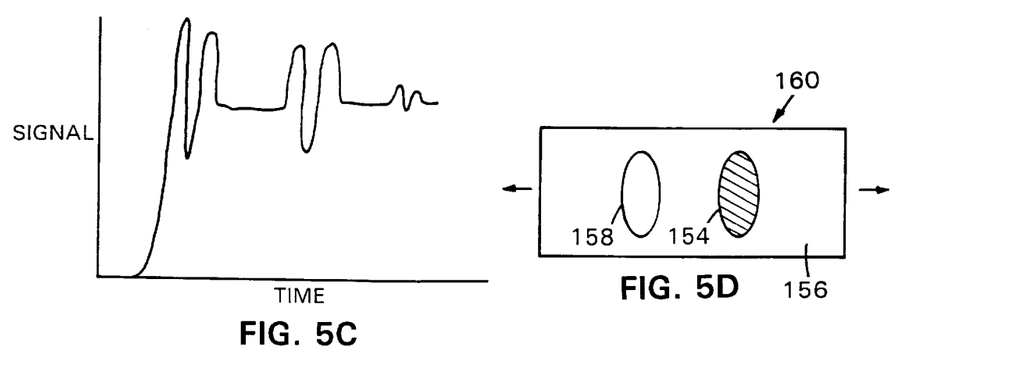
Figures 5E, 5F:
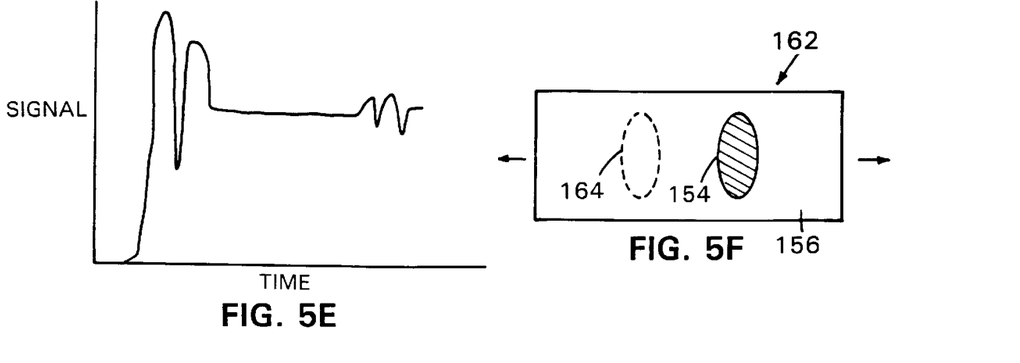

This example illustrates an analysis of a simplified thin film structure to determine the presence of defects. Referring to FIGS. 5A and 5B, an anticipated signal (FIG. 5A) measured by the film measuring device is shown for a thin film structure 150 (FIG. 5B) having two metal trenches 152 and 154 embedded in an oxide 156. Following the initial peak at t=0, two subsequent peaks should be observed at later times corresponding to a partial reflection of the wavepacket (i.e., an echo) from each of the two trenches. Multiple reflections may also contribute to the signal. However, to a first approximation, only echoes from a single reflection need to be considered since the echo amplitude will diminish with each partial reflection. Furthermore, the second peak should be somewhat smaller than the first peak since the amplitude of the acoustic wavepacket at the second trench is reduced due to the partial reflection by the first trench. Finally, the round trip time of the echoes can indicate the location of the trenches relative to the excitation and probe beams. The signal in FIG. 5A is the reference signal for a defect free structure of the type shown in FIG. 5B.

Defects can form in structures of this type during processing. For example, a region which is suppose to be filled with metal may be empty, e.g., contains neither metal nor oxide. Other types of defects may include improperly spaced features, or features in which several materials, e.g., several metal layers, are intended but are not all present. A feature or part of a feature may be missing, so that, for example, a region within an oxide layer that is intended to be metal filled is instead continuous oxide.

Referring to FIGS. 5C–5F, if a test structure 160 actually had a void 158 (i.e., an unfilled cavity) where the first trench was expected (FIG. 5D), the measured response (FIG. 5C) would be different than the anticipated response. In particular, the first echo would be much larger than anticipated since there is a much larger acoustic impedance mismatch between oxide and air, than between oxide and polysilicon. If instead, the test structure 162 lacked even a cavity 164 where the first trench was expected (FIG. 5F), the acoustic wavepacket would see continuous oxide and the response (FIG. 5E) would include only a single echo peak corresponding to the "second" trench 154. Other permutations follow in a straightforward way from these examples.

Light Sources

Suitable lasers for the excitation light source include, among others, Nd:YLF, ion (e.g., argon and krypton), Ti:Sapphire, diode, $CO_2$, holmium, excimer, dye, and metal-vapor lasers. Typically, these lasers are electro-optically or acousto-optically modulated (using, e.g., mode-locking and Q-switching devices known in the art) to produce suitable energies (i.e., between 0.1 microjoule/pulse and 50 millijoules/pulse) and pulse durations (i.e., less than about 1 ns, and sometimes less than 0.1 ns). Another suitable excitation light source is a microchip laser, such as described in U.S. Pat. No. 5,394,413. If the fundamental frequency of the light source is lower than the absorption frequency of the film, the light may be passed through a non-linear optical media to generate light at a higher energy. If the wavelengths of the two excitation pulses are such that the pulses are attenuated by the beam-splitting optics, the order of the harmonic generation and beam splitting may be reversed, i.e., two pulses of the fundamental frequency are first generated, and then each pulse is independently passed through a non-linear optical device (or devices) to increase the frequency. In addition, the repetition rate of the pulses must be high enough to allow suitable data averaging, but low enough to allow the thermal properties of the film to recover between laser shots. Light sources for the probe laser may include diode, argon ion, and krypton ion lasers, as well as pulsed or mode-locked light sources including Q-switched Nd:YAG, Nd:YLF, Ti:Sapphire, diode, $CO_2$, holmium, excimer, dye, and metal-vapor lasers.

In addition to the elements described previously for directing the excitation and probe pulses onto the sample, other optical systems can be used. One such system, for example, is described in U.S. Ser. No. 08/377,310, Rogers et al., entitled "Simplified Device and Method for Time-resolved Optical Measurements", filed Jan. 24, 1995, the contents of which are incorporated herein by reference. The optical system described in this reference includes a "phase mask" that diffracts a single, incident excitation beam into two spatially diverging beams; the angle of divergence is determined by a diffraction pattern on the phase mask. Using a lens, the diverging beams are recombined and imaged onto a sample's surface, where they interfere to form the excitation pattern having a well-defined wave-vector (i.e., the grating pattern). Excitation patterns having different wavevectors are formed simply by translating the phase mask to move different diffracting patterns into the excitation beam's path.

Furthermore, in some cases, the exposed region of a thin film structure may contain a repeating pattern of features such as strips. Then crossed pulses may not be necessary for acoustic wave excitation. A single beam incident upon such a pattern will undergo different amounts of absorption in the different regions, resulting in differential heating and thermal expansion. This will launch acoustic waves. It may not be necessary for the pattern to be spatially periodic. It may be advantageous to use this method since then, if the features have "sharp" edges, there will be acoustic wave components with very short wavelengths (i.e. high wavevectors) and this will improve the spatial resolution of the measurement.

In general, the excitation pattern of light may be other than spatially periodic. For example, a single spot or line of excitation light may be used, or a pattern may be used which yields higher sensitivity to a particular pattern of features. The excitation pattern may be optimized to maximize the affects of anticipated defects on signal features.

Other embodiments are also in the scope of the invention. For example, although in our examples diffraction of the probe beam is measured in the backward direction, diffraction of the probe beam can also be measured in the forward direction, in which case the diffracted beam is transmitted through the thickness of the structure before being measured. Also, the method can be used off-line when measurement time constraints are less demanding than during in-line use. Finally, the probe beam spot size can be made very large, and the diffraction of the probe beam spatially resolved using an array detector. This allows information about multiple locations of the film to be recorded simultaneously.

Other aspects, advantages, and modifications are within the scope of the following claims.

What is claimed is:

1. A method for detecting a subsurface defect in a thin film, comprising:

optically generating an acoustic wave in the film by exciting the film with a pair of crossed excitation pulses;

diffracting light from a time-dependent reflection of the acoustic wave caused by subsurface features in the film to produce a time-dependent signal; and analyzing the time-dependent signal to detect an existence of the defect based on the time-dependent reflection.

2. The method of claim 1, wherein the analyzing step comprises comparing the signal to a reference signal for a defect-free film.

3. The method of claim 2, wherein the comparing step comprises:

normalizing a portion of the signal to a corresponding portion of the reference signal, wherein the portions each comprise values at a series of time points;

calculating a difference in the values of the portions at each of the time points; and summing squares of the differences to determine an effective value for the similarity of the film to the defect-free film.

4. The method of claim 2, wherein the comparing step comprises:

normalizing a portion of the signal to a corresponding portion of the reference signal, wherein the portions each comprise values at a series of time points;

Fourier transforming each of the portions to produce transformed portions comprising values at a series of frequency points;

calculating a difference in the values of the transformed portions at each of the frequency points; and summing squares of the differences to determine an effective value for the similarity of the film to the defect-free film.

5. The method of claim 1, further comprising:

determining the position of the defect from the signal.

6. The method of claim 1, wherein the generating step includes producing counter-propagating acoustic waves.

7. The method claim 1, wherein the laser pulses have pulse durations of less than about 1 ns.

8. The method claim 1, wherein the laser pulses have pulse durations of less than about 150 ps.

9. The method of claim 1, wherein the generating step comprises passing a beam through a mask to produce the pair of crossed laser pulses used to excite the film.

10. The method of claim 1, wherein the light is diffracted from an area of the film excited by the pair of crossed excitation pulses.

11. The method of claim 1, wherein the subsurface defect is a void in a trench.

12. The method of claim 1, wherein the subsurface defect is an absence of a trench.

13. The method of claim 1, wherein the subsurface defect is a void in a post.

14. The method of claim 1, wherein the subsurface defect is an absence of a post.

15. A method for detecting a subsurface defect in a thin film, comprising:

optically generating an acoustic wave in a first spatial region of the film;

optically measuring a time-dependent reflection of the acoustic wave from subsurface features in the film to produce a time-dependent signal; and analyzing the signal to detect an existence of the defect by comparing the signal to a reference signal for a defect-free film, wherein comparing comprises:

normalizing a portion of the signal to a corresponding portion of the reference signal, wherein the portions each comprise values at a series of time points;

calculating a difference in the values of the portions at each of the time points; and     summing squares of the differences to determine an effective value for the similarity of the film to the defect-free film.

16. A method for detecting a subsurface defect in a thin film, comprising:

optically generating an acoustic wave in a first spatial region of the film;

optically measuring a time-dependent reflection of the acoustic wave from subsurface features in the film to produce a time-dependent signal; and analyzing the signal to detect an existence of the defect by comparing the signal to a reference signal for a defect-free film, wherein comparing comprises:normalizing a portion of the signal to a corresponding portion of the reference signal, wherein the portions each comprise values at a series of time points;

Fourier transforming each of the portions to produce transformed portions comprising values at a series of frequency points;

calculating a difference in the values of the transformed portions at each of the frequency points; and summing squares of the differences to determine an effective value for the similarity of the film to the defect-free film.

\* \* \* \* \*

UNITED STATES PATENT AND TRADEMARK OFFICE
CERTIFICATE OF CORRECTION

PATENT NO.     : 5,982,482
DATED          : NOVEMBER 9, 1999
INVENTOR(S)    : KEITH A. NELSON, JOHN A. ROGERS

It is certified that error appears in the above-identified patent and that said Letters Patent is hereby corrected as shown below:

Col. 1, line 7, "DMR-900279" should be --DMR-9317198--.

Signed and Sealed this

Twenty-eighth Day of November, 2000

Attest:

Attesting Officer

Q. TODD DICKINSON
Director of Patents and Trademarks